(12) United States Patent
Van Vliet et al.

(10) Patent No.: US 10,845,360 B2
(45) Date of Patent: Nov. 24, 2020

(54) NEURONAL AXON MIMETICS FOR IN VITRO ANALYSIS OF NEUROLOGICAL DISEASES, MYELINATION, AND DRUG SCREENING

(71) Applicants: Massachusetts Institute of Technology, Cambridge, MA (US); President and Fellows of Harvard College, Cambridge, MA (US)

(72) Inventors: Krystyn J. Van Vliet, Lexington, MA (US); Anna Jagielska, Topsfield, MA (US); Kimberly Homan, Somerville, MA (US); Jennifer A. Lewis, Cambridge, MA (US); Travis Alexander Busbee, Somerville, MA (US)

(73) Assignees: Massachusetts Institue of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/387,323

(22) Filed: Apr. 17, 2019

(65) Prior Publication Data
US 2019/0242878 A1    Aug. 8, 2019

Related U.S. Application Data

(62) Division of application No. 15/442,530, filed on Feb. 24, 2017, now abandoned.

(60) Provisional application No. 62/299,964, filed on Feb. 25, 2016.

(51) Int. Cl.
*G01N 33/50* (2006.01)
*C12M 1/12* (2006.01)
*C12M 1/34* (2006.01)

(52) U.S. Cl.
CPC ......... *G01N 33/5032* (2013.01); *C12M 25/04* (2013.01); *C12M 25/14* (2013.01); *C12M 41/38* (2013.01); *C12M 41/46* (2013.01); *G01N 33/5058* (2013.01)

(58) Field of Classification Search
None
See application file for complete search history.

(56) References Cited

U.S. PATENT DOCUMENTS

| | | | |
|---|---|---|---|
| 9,072,592 B2 | 7/2015 | Park et al. | |
| 9,512,404 B2 | 12/2016 | Stupp et al. | |
| 2004/0009593 A1 | 1/2004 | Keirstead et al. | |
| 2007/0099294 A1 | 5/2007 | Yang et al. | |
| 2014/0134729 A1 | 5/2014 | Shogbon et al. | |
| 2016/0067375 A1 | 3/2016 | Holmes et al. | |
| 2016/0089837 A1 | 3/2016 | Hsi et al. | |
| 2016/0251646 A1 | 9/2016 | Guire et al. | |
| 2017/0072105 A1 | 3/2017 | Jeffries et al. | |
| 2017/0328888 A1 | 11/2017 | Van Vliet et al. | |
| 2018/0327715 A1 | 11/2018 | Espinosa-Hoyos et al. | |

FOREIGN PATENT DOCUMENTS

| | | |
|---|---|---|
| CN | 105631930 A | 6/2016 |
| CN | 105711099 A | 6/2016 |
| CN | 106039417 A | 10/2016 |
| CN | 106215245 A | 12/2016 |
| CN | 106283216 A | 1/2017 |
| CN | 106492273 A | 3/2017 |
| GB | 2397824 A | 8/2004 |
| KR | 101622054 B1 | 5/2016 |
| WO | WO 2003/070171 A3 | 8/2003 |
| WO | WO 2004/094586 A2 | 11/2004 |
| WO | WO 2013/074972 A1 | 5/2013 |
| WO | WO 2013/172831 A1 | 11/2013 |
| WO | WO 2014/100199 A1 | 6/2014 |
| WO | WO 2014/116946 A1 | 7/2014 |
| WO | WO 2015/048355 A1 | 4/2015 |
| WO | WO 2016/077551 A1 | 5/2016 |
| WO | WO 2016/168485 A1 | 10/2016 |
| WO | WO 2016/192733 A1 | 12/2016 |
| WO | WO 2016/196774 A1 | 12/2016 |
| WO | WO 2017/017003 A1 | 2/2017 |
| WO | WO 2017/147501 A1 | 8/2017 |
| WO | WO 2018/208909 A1 | 11/2018 |

OTHER PUBLICATIONS

Espinosa-Hoyos et al., Engineered 3D-printed artificial axons, Jan. 11, 2018, Scientific Reports 8:478 | DOI:10.1038/s41598-017-18744-6, 13 pages (Year: 2018).*

Hobzova et al., Embedding of Bacterial Cellulose Nanofibers within PHEMA Hydrogel Matrices: Tunable Stiffness Composites with Potential for Biomedical Applications, 2018, Journal of Nanomaterials vol. 2018, Article ID 5217095, 11 pages (Year: 2018).*

Rosser et al., Recent Advances of Biologically Inspired 3D Microfluidic Hydrogel Cell Culture Systems, 2015, . J Cell Biol Cell Metab 2: 005, 34 pages (Year: 2015).*

Aoun, L. et al., "Microdevice arrays of high aspect ratio Poly(DiMethylSiloxane) pillars for the investigation of multicellular tumour spheroid mechanical properties," Lab Chip 14(13): 2344-2353 (2014).

Arulmoli, J. et al., "Static stretch affects neural stem cell differentiation in an extracellular matrix-dependent manner," Sci. Rep. 5: 8499 1-8 (2015).

Baker, B. et al., "Cell-mediated fiber recruitment drives extracellular matrix mechanosensing in engineered fibrillar microenvironments," Nat. Mater. 14(12): 1262-1268 (2015).

(Continued)

*Primary Examiner* — John D Ulm
(74) *Attorney, Agent, or Firm* — Hamilton, Brook, Smith & Reynolds, P.C.

(57) ABSTRACT

Aspects of the present invention provide improved methods and apparatus for use in in vitro modeling of the interaction of cells with cellular constructs/parts/axons, including axon mimetics and use of three-dimensional fibers.

27 Claims, 10 Drawing Sheets
(6 of 10 Drawing Sheet(s) Filed in Color)

(56) References Cited

OTHER PUBLICATIONS

Baker, S. et al., "Determining the mechanical properties of electrospun poly-ε-caprolactone (PCL) nanofibers using AFM and a novel fiber anchoring technique," Mater. Sci. Eng. C 59: 203-212 (2016).
Barry, R. et al., "Direct-Write Assembly of 3D Hydrogel Scaffolds for Guided Cell Growth," Adv. Mater., 21(23): 2407-2410 (2009).
Bechler, M. et al., "CNS Myelin Sheath Lengths are an Intrinsic Property of Oligodendrocytes," Curr. Biol. 25: 2411-2416 (2015).
Bradel, E. et al., "Cultured neonatal rat oligodendrocytes elaborate myelin membrane in the absence of neurons," J. Neurosci. Res. 9: 381-392 (1983).
Bullock, P. et al., "Glass micro-fibers: a model system for study of early events in myelination," J. Neurosci. Res. 27: 383-393 (1990).
Chandra, D., "Capillary Force in High Aspect-Ratio Micropillar Arrays," University of Pennsylvania, ProQuest Dissertations Publishing (2009).
Chong, S. et al., "Neurite outgrowth inhibitor Nogo-A establishes spatial segregation and extent of oligodendrocyte myelination," Proc. Natl. Acad. Sci. 109(4): 1299-1304 (2012).
Christ, A. et al., "Mechanical difference between white and gray matter in the rat cerebellum measured by scanning force microscopy," J. Biomech. 43(15): 2986-2992 (2010).
Dinis, T. et al., "3D multi-channel bi-functionalized silk electrospun conduits for peripheral nerve regeneration," Journal of the Mechanical Behavior of Biomedical Materials, 41: 43-55 (2015).
Espinosa-Hoyos, D. et al., "Poly(HDDA)-Based Polymers for Microfabrication and Mechanobiology," Biomaterials and Soft Materials 2(24): 1315-1321 (2017).
Franklin, R., "Why does remyelination fail in multiple sclerosis?," Nat. Rev. Neurosci. 3: 705-714 (2002).
Franze, K. et al., "Mechanics in neuronal development and repair," Annu. Rev. Biomed. Eng. 15: 227-251 (2013).
Friese, M. et al., "Acid-sensing ion channel-1 contributes to axonal degeneration in autoimmune inflammation of the central nervous system," Nat. Med. 13: 1483-1489 (2007).
Gardner, A. et al., "Myelination of rodent hippocampal neurons in culture," Nat. Protoc. 7(10): 1774-1782 (2012).
Ghasemi-Mobarakeh L. et al., "Electrical stimulation of nerve cells using conductive nanofibrous scaffolds for nerve tissue engineering," Tissue Engineering Part A, 15(11): 3605-3619 (2009).
Gratson, G. et al., "Microperiodic structures: Direct writing of three-dimensional webs," Nature 428: 386 (2004).
Hanson-Shepherd, J. et al., "3D Microperiodic Hydrogel Scaffolds for Robust Neuronal Cultures," Adv. Funct. Mater., 21(1): 47-54 (2011).
Hardin, J. et al., "Microfluidic printheads for multimaterial 3D printing of viscoelastic inks," Adv. Mater. 27: 3279-3284 (2015).
Harlow, D. et al., "Inhibitors of myelination: ECM changes, CSPGs and PTPs," Exp. Neurol. 251: 39-46 (2014).
Hernandez, M. et al., "Mechanostimulation promotes nuclear and epigenetic changes in oligodendrocytes," J. Neurosci. 36(3): 806-813 (2016).
Hildebrand, C. et al., "Myelinated nerve fibres in the CNS," Prog. Neurobiol. 40: 319-384 (1993).
Hutter, J. et al., "Calibration of atomic-force microscope tips," Rev. Sci. Instrum. 64(7): 1868-1873 (1993).
International Search Report and Written Opinion dated Jun. 12, 2017 for International Application No. PCT/US2017/019463, entitled "Neuronal Axon Mimetics for In Vitro Analysis of Neurological Diseases, Myelination, and Drug Screening."
International Search Report and Written Opinion dated Aug. 22, 2018 for International Application No. PCT/US2018/031792, entitled "Cell-Mimetic Device".
Jagielska, A. et al., "Extracellular Acidic pH Inhibits Oligodendrocyte Precursor Viability, Migration, and Differentiation," PLoS ONE, 8(9): 1-13 (2013).
Jagielska, A. et al., "Mechanical Environment Modulates Biological Properties of Oligodendrocyte Progenitor Cells," Stem Cells & Dev., 21(16): 2905-2914 (2012).

Jarjour, A. et al., "In vitro modeling of central nervous system myelination and remyelination," Glia 60(1): 1-12 (2012).
Jeong, S. et al., "Development of electroactive and elastic nanofibers that contain polyaniline and poly(L-lactide-co-epsilon-caprolactone) for the control of cell adhesion," Macromol Biosci 8: 627-637 (2008).
Kador, K. et al., "Control of Retinal Ganglion Cell Positioning and Neurite Growth: Combining 3D Printing with Radial Electrospun Scaffolds," Tissue Engineering—Part A, 22(3-40): 286-294 (2016).
Kerman, B. et al., "In vitro myelin formation using embryonic stem cells," Development, 142: 2213-2225 (2015).
Kippert, A. et al., "Actomyosin contractility controls cell surface area of oligodendrocytes," BMC Cell Biology 10:71 (2009).
Kohlschütter, A. et al., "Childhood leukodystrophies: A clinical perspective," Expert Review of Neurotherapeutics, 11(10): 1485-1496 (2011).
Kolesky, D. et al., "3D Bioprinting of Vascularized, Heterogeneous Cell-Laden Tissue Constructs," Adv. Mater., vol. 26, Issue 19, 3124-3130 (2014).
Kolesky, D. et al., "Three-dimensional bioprinting of thick vascularized tissues," Proceedings of the National Academy of Sciences, 113(12): 3179-3184 (2016).
Kotwal, A. et al., "Electrical stimulation alters protein adsorption and nerve cell interactions with electrically conducting biomaterials," Biomaterials 22: 1055-1064 (2001).
Lakhani, B. et al., "Hemispheric asymmetry in myelin after stroke is related to motor impairment and function," NeuroImage Clinic, 14: 344-353 (2017).
Lariosa-Willingham, K. et al., "Development of a central nervous system axonal myelination assay for high throughput screening," BMC Neuroscience, 17: 16 (2016).
Lee, H. et al., "Direct alignment and patterning of silver nanowires by electrohydrodynamic jet printing," Small 10: 3918-3922 (2014).
Lee, M. et al., "Development of a 3D printer using scanning projection stereolithography," Scientific Reports, 5: 9875 (2015).
Lee, S. et al., "A culture system to study oligodendrocyte myelination processes using engineered nanofibers," Nature Methods, 9(9): 917-922 (2012).
Lee, S. et al., "A rapid and reproducible assay for modeling myelination by oligodendrocytes using engineered nanofibers," Nat. Protoc. 8, 771-782 (2013).
Lee, S. et al., "Fabrication of a Highly Aligned Neural Scaffold via a Table Top Stereolithography 3D Printing and Electrospinning," Tissue Engineering Part A, 23(11-12): 491-502 (2017).
Levental, I. et al., "Soft biological materials and their impact on cell function," Soft Matter, 3: 299-306 (2007).
Li, M. et al., "Electrospinning polyaniline-contained gelatin nanofibers for tissue engineering applications," Biomaterials, 27: 2705-2715 (2006).
Li, Y. et al., "Nanofibers support oligodendrocyte precursor cell growth and function as a neuron-free model for myelination study," Biomacromolecules, 15(1): 319-326 (2014).
Liewald, D. et al., "Distribution of axon diameters in cortical white matter: an electron-microscopic study on three human brains and a macaque," Biological Cybernetics. 108(5): 541-557 (2014).
International Preliminary Report on Patentability dated Aug. 28, 2018 for International Application No. PCT/US2017/019463, entitled "Neuronal Axon Mimetics for In Vitro Analysis of Neurological Diseases, Myelination, and Drug Screening."
Liu, C. et al., "Novel electrospun polylactic acid nanocomposite fiber mats with hybrid graphene oxide and nanohydroxyapatite reinforcements having enhanced biocompatibility," Polymers (Basel), 8: 287-306 (2016).
Liu, Y. et al., "3D bio-nanofibrous PPy/SIBS mats as platforms for cell culturing," Chemical Communications, 32: 3729-3731 (2008).
Lourenço, T. et al., "Modulation of Oligodendrocyte Differentiation by Mechanotransduction," Front Cell Neurosci., 10: 277 (2016).
Lu, Y. et al., "A digital micro-mirror device-based system for the microfabrication of complex, spatially patterned tissue engineering scaffolds," J. Biomed. Mater. Res. Part A, 77A: 396-405 (2006).
Lu, Y. et al., "Viscoelastic properties of individual glial cells and neurons in the CNS," Proc. Natl. Acad. Sci., 103(47): 17759-17764 (2006).

(56) References Cited

OTHER PUBLICATIONS

Malda, J. et al. "25th anniversary article: engineering hydrogels for biofabrication," Adv. Mater., 25(36): 5011-5028 (2013).
Martin, R. et al., "Electrospinning 3D scaffolds for use in neural tissue engineering," Materials Research Society Symposium Proceedings, 1798: 13-18 (2015).
Mccarthy, K. et al., "Preparation of separate astroglial and oligodendroglial cell cultures from rat cerebral tissue," J. Cell Biol., 85: 890-902 (1980).
Mei, F. et al., "Micropillar arrays as a high-throughput screening platform for therapeutics in multiple sclerosis," Nat. Med., 20, 954-960 (2014).
Merolli, A., et al., "The use of a suspended carbon fiber culture to model myelination by human Schwann cells," J Mater Sci: Mater Med., 28:57 (2017).
Miller, K. et al., "Mechanical properties of brain tissue in-vivo: experiment and computer simulation," J. Biomech., 33: 1369-1376 (2000).
Moeendarbary, E. et al., "The soft mechanical signature of glial scars in the central nervous system," Nat. Commun., 8(14787) (2017).
Murphy, M. et al., "Decreased brain stiffness in Alzheimer's disease determined by magnetic resonance elastography," J. Magn. Reson. Imaging 34: 494-498 (2011).
Murphy, M. et al., "Regional brain stiffness changes across the Alzheimer's disease spectrum," NeuroImage. Clin., 10: 283-290 (2016).
Ortega, I. et al., "Fabrication of biodegradable synthetic perfusable vascular networks via a combination of electrospinning and robocasting," Biomater. Sci., 3: 592-596 (2015).
Othon, C. et al., "Single-cell printing to form three-dimensional lines of olfactory ensheathing cells," Biomed. Mater. 3(3) (2008).
Pai, C., "Morphology and mechanical properties of electrospun polymeric fibers and their nonwoven fabrics," Massachusetts Institute of Technology, Dept. of Chemical Engineering (2011).
Palchesko, R. et al., "Development of Polydimethylsiloxane substrates with turnable elastic modulus to study cell mechanobiology in muscle and nerve," PLoS ONE, 7(12): 1-13 (2012).
Pan, Y., "Study of separation force in constrained surface projection stereolithography," Rapid Prototyp. J., 23(2): 353-361 (2017).
Pang, Y. et al., "Neuron-oligodendrocyte myelination co-culture derived from embryonic rat spinal cord and cerebral cortex," Brain Behavior, 2: 53-67 (2012).
Riek, K. et al., "Magnetic resonance elastography reveals altered brain viscoelasticity in experimental autoimmune encephalomyelitis," NeuroImage Clin. 1: 81-90 (2012).
Rosenberg, S. et al., "The geometric and spatial constraints of the microenvironment induce oligodendrocyte differentiation," Proc. Natl. Acad. Sci., 105(38): 14662-14667 (2008).
Schmidt, C. et al., "Stimulation of neurite outgrowth using an electrically conducting polymer," Proceedings of the National Academy of Sciences of the USA, Applied Biological Sciences, 94: 8948-8953 (1997).
Schregel, K. et al., "Demyelination reduces brain parenchymal stiffness quantified in vivo by magnetic resonance elastography," Proc. Natl. Acad. Sci., 109: 6650-6655 (2012).
Shah, S. et al., "Guiding stem cell differentiation into oligodendrocytes using graphene-nanofiber hybrid scaffolds," Adv. Mater., 26: 3673-3680 (2014).
Shi, G. et al., "Electrical stimulation enhances viability of human cutaneous fibroblasts on conductive biodegradable substrates," J Biomed. Mater Res. Part A, 84A: 1026 (2007).
Shim, J. et al., "Development of a hybrid scaffold with synthetic biomaterials and hydrogel using solid freeform fabrication technology," Biofabrication, 3, 034102: 1-9 (2011).
Shimizu, T. et al., "YAP functions as a mechanotransducer in oligodendrocyte morphogenesis and maturation," Glia, 65: 360-374 (2017).
Silva, E. et al., "Size Effects on the Stiffness of Silica Nanowires," Small, 2: 239-243 (2006).
Singh, V. et al., "Scalable Fabrication of Low Elastic Modulus Polymeric Nanocarriers With Controlled Shapes for Diagnostics and Drug Delivery," J. Micro Nano-Manufacturing, 3, 011002 (2015).
Smoukov, S. et al., "Scalable Liquid Shear-Driven Fabrication of Polymer Nanofibers," Advanced Materials, 27(16): 2642-2647 (2015).
Sobel, R. et al., "Fibronectin in multiple sclerosis lesions," Am. J. Pathol., 135(1): 161-168 (1989).
Stoffels, J. et al., "Fibronectin aggregation in multiple sclerosis lesions impairs remyelination," Brain, 136: 116-131 (2013).
Sun, C. et al., "Projection micro-stereolithography using digital micro-mirror dynamic mask," Sensors and Actuators A, 121: 113-120 (2005).
Sur, S. et al., "Tuning supramolecular mechanics to guide neuron development," Biomaterials, 34(20): 4749-4757 (2013).
Tkachev, D. et al., "Oligodendrocyte dysfunction in schizophrenia and bipolar disorder," Lancet, 362: 798-805 (2003).
Tuck, S., "Critical variables in the alignment of electrospun PLLA nanofibers," Materials Science & Engineering C, Biomimetic and Supramolecular Systems, 32(7): 1779-84 (2012).
Tumbleston, J. et al., "Continuous liquid interface production of 3D objects," Science, 347(6228): 1349-1352 (2015).
Urbanski, M. et al., "Myelinating glia differentiation is regulated by extracellular matrix elasticity," Scientific Reports, 6: 33751 (2016).
Valentini, R. et al., "Electrically charged polymeric substrates enhance nerve fibre outgrowth in vitro," Biomaterials 13(3): 183-190 (1992).
Wu, Y. et al., "Alterations of myelin morphology and oligodendrocyte development in early stage of Alzheimer's disease mouse model," Neuroscience Letters, 642: 102-106 (2017).
Yu, L. et al., "Promoting neuron adhesion and growth," MaterialsToday, 11(5): 36-43 (2008).
Zeiger, A., "Chemomechanics at Cell-Cell and Cell-Matrix Interfaces Critical to Angiogenesis," Department of Materials Science and Engineering, Massachusetts Institute of Technology (2013).
Zheng, X et al., "Ultralight, Ultrastiff Mechanical Metamaterials," Science, 344(6190): 1373-1377 (2014).
Huang, J. et al., "Electrical regulation of Schwann cells using conductive polypyrrole/chitosan polymers," J Biomed Mater. Res. Part A 93(1): 164-74 (2010).
Jagielska, A. et al., "Mechanical strain promotes oligodendrocyte differentiation by global changes of gene expression," Front. Cell. Neurosci. 11, 93 (2017), 16 pages.
Howe, C. L. "Coated Glass and Vicryl Microfibers as Artificial Axons," Cells Tissues Organs 183, 180-194 (2006).
Non-Final Office Action for U.S. Appl. No. 15/442,530, titled: Neuronal Axon Mimetics for In Vitro Analysis of Neurological Diseases, Myelination, and Drug Screening, dated Dec. 17, 2018.
Homan, K. et al., "3D Printing of Hydrogel Scaffolds with Tailored Composition and Stiffness," Harvard School of Engineering, Wyss Institute, 1 page, (2014). (Reference 25).
International Preliminary Report on Patentability dated Nov. 12, 2019 for International Application No. PCT/US2018/031792; Entitled "Engineered 3D-Printed Artificial Axons"; consisting of 8 pages.
Raredon, M., "Design and fabrication of physiologic tissue scaffolds using projection-micro-stereolithography," Massachusetts Institute of Technology, Dept. of Materials Science and Engineering, 68 pages, (2014). (Reference 72).
Roussos, P. et al., "Schizophrenia: susceptibility genes and oligodendroglial and myelin related abnormalities," Front. Cell. Neurosci. 8(5), 7 pages, (2014). (Reference 75).
Streitberger, K. et al., "Brain viscoelasticity alteration in chronic-progressive multiple sclerosis," PLoS One, 7(1): e29888, 7 pages, (2012). (Reference 87).
Sun, L. et al., "Direct-Write Assembly of 3D Silk/Hydroxyapatite Scaffolds for Bone Co-Cultures," Advanced Healthcare Materials, 1(6): 729-735 (2012). (Reference 89).
Xanofi, Inc. http://xanofi.com/news/worlds-first-3d-polymer-nanofiber-scaffolding-printer/ 2 pages, (2014). (Reference 97).
Xia, C. et al., "Solvent-driven polymeric micro beam device," J. Micromechanics Microengineering, 20(8), 7 pages, (2010). (Reference 98).

(56) References Cited

OTHER PUBLICATIONS

Xu, W. et al., "Organic core-sheath nanowire artificial synapses with femtojoule energy consumption," Science Advances, 2(6): e1501326 (2016), 8 pages. (Reference 99).

Espinosa-Hoyos et al, Published online Jan. 11, 2018, Engineered 3D-printed artificial axons, Scientific Reports 8:4781 DOI: 10.1038/s41598-017-18744-6, 13 pages (2018). (Reference 104).

* cited by examiner

GRADIENT OF
FIBER DIAMETER

D1  D2  D3

GRADIENT OF
FIBER STIFFNESS

E1 E2 E3

NEURONAL AXON MIMETICS FOR IN VITRO ANALYSIS OF NEUROLOGICAL DISEASES, MYELINATION, AND DRUG SCREENING

RELATED APPLICATIONS

This application is a divisional of U.S. application Ser. No. 15/442,530, filed on Feb. 24, 2017, which claims the benefit of U.S. Provisional Application No. 62/299,964, filed on Feb. 25, 2016. The entire teachings of the above applications are incorporated herein by reference.

BACKGROUND

Currently, devices available to study neural cell responses are comprised chiefly of either two-dimensional (2D), stiff polystyrene tissue culture dishes or organotypic culture using tissue slices. There can be certain limitations to both approaches. The first format can be limited, for example, in eliciting cell responses that are recapitulated in vivo, because the smooth, flat, stiff surface provides a very different environment from the 3D, topographically complex, and mechanically compliant neural tissue comprising a network of neuronal axons and other features. The latter format can represent in vivo environments more credibly, but there can still be inherent variability between tissue slices. Further, organotypic cultures may not afford systematic isolation of the individual physical and chemical cues, limiting its usefulness in facilitating understanding of the role of each in disease characteristics or in drug screening responses.

Although certain electrospun nanofibers have been described as a model to study myelination (Lee et al. 2012, Li et al., 2014), these fibers were made from stiff polymers (polystyrene or polycaprolactone), therefore providing very different mechanical cues than does the compliant environment characterizing the central nervous system (CNS) in vivo. Moreover, electrospinning techniques do not provide adequate control of fiber alignment and construct geometry, and thus are not applicable for building complex fiber architectures or for creating controlled chemical and mechanical gradients via arrangement of different fiber types. Accordingly, there is a need for new and improved methods and apparatus for use in in vitro modeling of the interaction of cells with cellular constructs, including nerve cells and axons.

SUMMARY

Aspects of the present invention address this need by providing improved methods and apparatus for use in in vitro modeling of the interaction of cells with cellular constructs/parts/axons.

In one embodiment, the invention relates to a cell-mimetic device comprising: a three dimensional structure comprising a plurality of fibers, said plurality of fibers having an average stiffness post-curing of between about 0.1 and about 300 kPa, and an average diameter of between about 0.1 and about 50 micrometers; and a support structure connected to the three dimensional structure.

In some embodiments, the invention further relates to one, or to combination of the following:

the stiffness is calculated as any of Young's modulus, bulk modulus, shear modulus, and dynamic modulus;

the post-curing stiffness is between about 0.1 and 100 kPa;

the post-curing stiffness is between about 0.1 and 10 kPa;

the post-curing stiffness is between about 0.1 and 1 kPa;

the average diameter is between about 0.1 and about 10 micrometers;

the average diameter is between about 0.1 and about 1 micrometers;

the post-curing stiffness is measured after equilibration in an aqueous solution buffered at pH 7.0-7.4;

the plurality of fibers are arranged as one or more piles in the three dimensional structure;

the fibers are formed of compliant polymers or hydrogels;

the support structure is formed of glass, polystyrene, tissue culture dish, tissue culture plate, or molded polydimethylsiloxane (PDMS);

the fibers are polyethylene glycol (PEG), polyhydroxyethylmethacrylate (pHEMA), polydimethylsiloxane (PDMS), polyacrylamide, hyaluronic methacrylate, or any viscoelastic polymer, or any derivative of the foregoing;

the fibers are modified by a surface ligand;

the average stiffness is constant over the three dimensional structure;

the average diameter is constant over the three dimensional structure;

the surface ligand density or type is constant over the three dimensional structure;

at least one of fiber diameter, fiber stiffness, surface ligand density, and surface ligand type varies along at least one dimension of the three dimensional structure, including, for example, fiber arrangements that create gradients of one or more of fiber diameter, fiber stiffness, surface ligand density, and surface ligand type;

the three dimensional structure represents at least one of a model of a tissue, and a model of neuronal axons; and the fibers in the three dimensional structure are formed of a stretchable fiber material, optionally wherein any one or a combination of the following is true: (a) the stretchable fiber material is PDMS, pHEMA, hyaluronic methacrylate, or any viscoelastic polymer; (b) the three dimensional structure can be elastically deformed in at least one dimension by at least 5%; and (c) the device further comprises a substrate material attached to, and at least as elastically deformable in the at least one dimension as, the three dimensional structure.

In some embodiments, the invention relates to a method of studying cells in vitro, comprising: providing a three dimensional structure comprising a plurality of fibers, said plurality of fibers having an average stiffness post-curing of between about 0.1 and about 300 kPa, and an average diameter of between about 0.1 and about 50 micrometers; and a support structure connected to the three dimensional structure; providing a cell-mimetic device comprising a three dimensional structure comprising a plurality of fibers; contacting the cell-mimetic device with a population of cells; studying at least one feature of an interaction of the population of cells with the cell mimetic device; and studying at least one feature of an interaction between cells (either of the same cell type or of different cell types) within the cell-mimetic device.

In some embodiments, the invention further relates to one or any combination of the following:

the cells are neural cells;

the cells are oligodendrocytes; and the at least one feature of the interaction is production of myelin by the oligodendrocytes.

In some embodiments, the invention relates to a method of manufacturing a cell-mimetic device, comprising: creating a three dimensional structure comprising a plurality of fibers, the fibers having an average stiffness of between about 0.1 and about 300.0 kPa; and an average diameter of between about 0.1 and about 50 micrometers; and optionally wherein one or both of the following are true: three dimensional printing (3DP) is used to create the three dimensional structure; and the three dimensional structure represents any of: a model of a tissue, and a model of neuronal axons.

In some embodiments, the invention relates to an assay device comprising: a substrate; a fiber support attached to the substrate; and a plurality of fibers, each of the plurality of fibers: having a length and spanning from the substrate to the fiber support such that each fibers is suspended in air or fluid along at least part of the fiber length, and the plurality of fibers having an average stiffness of between about 0.1 and about 300.0 kPa and an average diameter of between about 0.1 and about 50 micrometers.

In some embodiments, the invention further relates to one or any combination of the following:

the stiffness is calculated as any of Young's modulus, bulk modulus, shear modulus, and dynamic modulus;

the post-curing stiffness is between about 0.1 and 100 kPa;

the post-curing stiffness is between about 0.1 and 10 kPa;

the post-curing stiffness is between about 0.1 and 1 kPa;

the average diameter is between about 0.1 and about 10 micrometers;

the average diameter is between about 0.1 and about 1 micrometers;

the post-curing stiffness is measured after equilibration in an aqueous solution buffered at pH 7.0-7.4;

the plurality of fibers are arranged as one or more piles in the three dimensional structure;

the fibers are formed of compliant polymers or hydrogels;

the support structure is formed of: (a) glass, polystyrene, or molded polydimehtylsiloxane (PDMS); (b) a tissue culture dish or a tissue culture plate; (c) or combination of the foregoing;

the fibers are PEG, pHEMA, PDMS, polyacrylamide, hyaluronic methacrylate, or any viscoelastic polymer, or a derivative of any of the foregoing;

the fibers are modified by a surface ligand;

the average stiffness is constant over the three dimensional structure;

the average diameter is constant over the three dimensional structure;

the surface ligand density or type is constant over the three dimensional structure;

at least one of fiber diameter, fiber stiffness, surface ligand density, and surface ligand type varies along at least one dimension of the three dimensional structure, including, for example, fiber arrangements that create gradients of fiber diameter, fiber stiffness, surface ligand density, surface ligand type, or a combination of the foregoing.

the three dimensional structure represents at least one of a model of a tissue, and a model of neuronal axons; and the fibers in the three dimensional structure are formed of a stretchable fiber material.

In some embodiments, the invention relates to an assay method comprising: given any of the assay devices as described herein or above: contacting the assay device with a population of cells as described herein or above; and studying at least one feature of an interaction of the population of cells with any of the cell-mimetic devices recited herein or above, optionally wherein any one or a combination of the following is true: the cells are oligodendrocytes and the at least one feature of the interaction is myelination of the plurality of fibers; the studying comprises determining, for at least one of the plurality of fibers, both an extent of myelination along a longitudinal axis of the fiber and a thickness of myelin; the longitudinal extent and thickness of myelin are determined from a single microscopy image; and the interaction of cells with plurality of fibers is measured by factors secreted by cells or/and by analysis of cell gene expression.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION

Figure 1A:
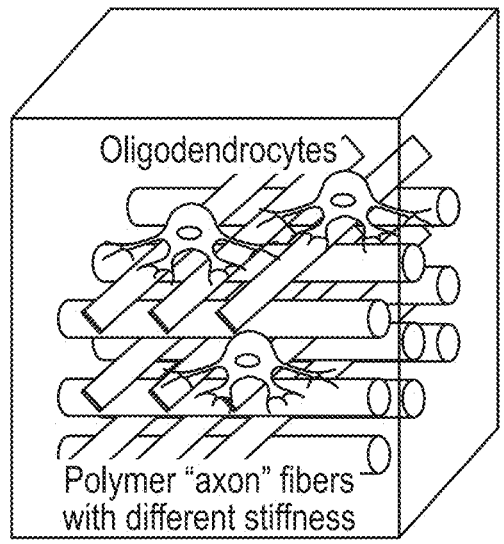
FIG. 1A depicts a device schematic, in accordance with aspects of the present invention, including, for this particular embodiment, a log-pile configuration of artificial axon fibers, and depicting an interaction of oligodendrocytes therewith.

For clarity of description, example embodiments are presented in the figures and below discussions. These examples are for purposes of illustration and not a limitation of the principles of the present invention. A description of example embodiments of the invention follows.

Cell-Mimetic Devices

The invention relates, in some embodiments, to the provision of cell-mimetic devices. As used herein a "cell-mimetic" is a structure that mimics one or more relevant features of a cell or a portion thereof. In some embodiments the cell mimetic is a "neuron-mimetic," mimicking features of a neuron (e.g, a peripheral neuron, a central nervous system (CNS) neuron, e.g., from brain or spinal cord). In some embodiments, the neuron-mimetic is an "axon-mimetic," mimicking a neuronal axon (e.g., a CNS neuronal axon).

Relevant Features

Relevant features of cells that can be mimicked by cell-mimetics include, without limitation: physical, mechanical, and biochemical properties and gradients of any of these properties. Physical properties include size, length, width, and density. Mechanical properties include stiffness. Biochemical properties include surface chemistry/ligand modification. Additional relevant properties may include biocompatibility and cell adherence. For example, it may be desirable for a neuron mimetic, or artificial axon, to be formed of materials that are biocompatible and cell adherent. These features can enable other cells such as glial cells from the CNS to be seeded within the mimetic, adhere, grow, and respond to cues such as administered drugs.

Form and Construction

Cell-mimetic devices can have a wide variety of forms. In some embodiments, they are comprised of groups of fibers (e.g., polymeric fibers) arranged in a desired 2D or 3D pattern. In some embodiments, the fibers are laid down by 3D printing. In some embodiments, axon mimetics are constructed to mimic one or more relevant features of neurons in the central nervous system ("neuron-mimetics").

Cell mimetics can be constructed of a wide variety of materials, including for example, polymers. As one example, neuron mimetics can be created by 3D printing, e.g., using a printing technique developed in the Lewis labs (Barry et al., 2009; Sun et al., 2012; Kolesky et al., 2014) that is specialized for printing of compliant materials at micrometer-scale dimensions. In some embodiments, this provides 3D mimetics of neuronal axons as defined by feature geometry, mechanical properties, and/or biochemical functionalization. In some embodiments, these devices enable neurological studies in both reductionist and complex environments, where individual cues can be studied separately or be considered together.

In some embodiments, 3D printing allows for one or a combination of the following: (a) creation of neuronal axon mimetics (artificial axons) having flexible design; (b) fabrication of multiple fiber geometries and structure architectures; and (c) the representation of particular biophysical microenvironments, including defined magnitudes and gradients of fiber mechanical stiffness, diameter, and/or ligand/molecule presentation at the fiber surface. One embodiment includes a stretchable version of the neuronal axon mimetic, to incorporate effects of mechanical strain and/or fiber diameter changes on the responses of the cell types adhered to those fibers.

3D-Printed Artificial Axons Device

For example, as described below, certain elements of this product and process include neuron mimetic devices consisting of multilayers of 3D-printed fibers, with varying diameters and spacing between fibers. In some embodiments, a cell-mimetic device (e.g., a neuron mimetic/3DP neuron mimetic/artificial axon device) consists of 3DP fibers (e.g., fibers mimicking neuronal axons) organized into multilayered structures (e.g., FIG. 1A). For example, as shown with respect to FIGS. 1A-1D (further discussed below), the fibers can have a diameter of 10 µm, and a tunable spacing between fiber centers in the range of 20-50 µm. There is also the capacity to print multimaterial devices, such as, for example, where fibers within the same array are printed with different materials (FIG. 1H) (e.g., up to four different materials).

The ability of oligodendrocyte precursor cells (OPCs)—which act in vivo to protect axons by wrapping them in a myelin sheath—to adhere, survive, migrate and differentiate into oligodendrocytes that produce myelin was confirmed in embodiments of the invention. OPCs thrived on these scaffolds, and were able to migrate along and between the fibers (FIG. 1E). After several days in culture within the neuron mimetic device, OPCs differentiated into oligodendrocytes that wrapped myelin around the fibers, remarkably similar to wrapping of axons that is observed in vivo (FIGS. 1F-G).

In some embodiments, neuron mimetic devices have multilayers of 3D-printed fibers with diameter of 5-10 µm, and tunable spacing between axon fiber centers (20-150 µm).

In some embodiments, devices according to the present invention have one, or any combination of, the following characteristics:

Fibers represent neuronal axons.

Fibers can be printed at various mechanical stiffnesses of the solid printed material, including a very low range of Young's elastic modulus E~0.1-1 kPa, corresponding to the low stiffness of mammalian neuronal axons, as well as higher stiffness, above 1 kPa, corresponding to neuron pathologies.

Controllable fiber diameters, within the range of 0.5-10 µm, are employed, being comparable to the diameters of neuronal axons.

Fiber surfaces can be functionalized with proteins representing extracellular matrix (ECM) components and ligands.

Multifiber, multilayer configurations are used to systematically position fiber axis orientations within and among multiple layers, allowing for formation of mechanical and biochemical gradients.

High optical transparency materials are used to enable observations of structures and cell-structure interactions via optical methods such as confocal microscopy.

A reductionist design is used to allow for isolating/studying individual biochemical and mechanical factors.

Design allows for additional components to be added, e.g., components characteristic of disease environment, such as other neural cell types, ECM proteins, growth factors, and variation of tissue stiffness, axon diameter, etc.

The system is permissible for fluids and gases.

Device allows for cell migration along and across the fibers.

Device allows for facile fluid/media exchange.

System is stable in biological conditions (e.g., one or more of 37° C., 5% $CO_2$, high salinity, and high humidity).

System can be made by an inexpensive manufacturing process that is amenable to rapid design changes in printed device features.

Individual devices can be easily multiplexed by printing in standard multi-well plates (e.g., from 6- to 384-well plates)

FIG. 1A shows a schematic of an example of a 3D-printed artificial axon device, showing fibers representing axons in a log-pile configuration, and oligodendrocytes interacting with artificial axon fibers.

Figure 1B:
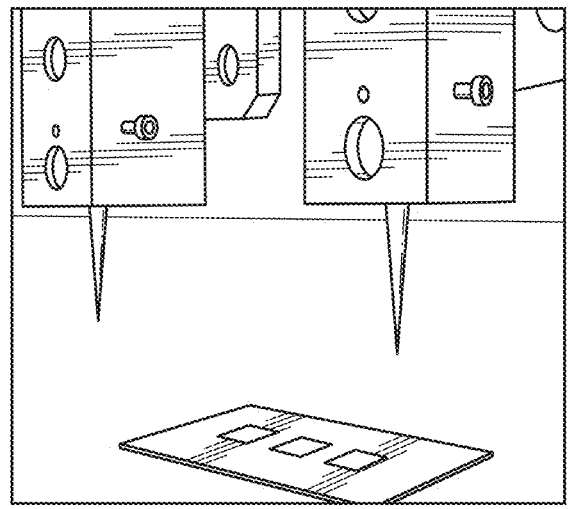
FIG. 1B depicts a process of 3D-printing on a glass slide, in accordance with aspects of the present invention.

FIG. 1B shows a process of 3D-printing devices on a glass slide. (Taken from "Organs on demand", The Scientist, Sep. 1, 2013, courtesy of J. A. Lewis.)

Figure 1C:
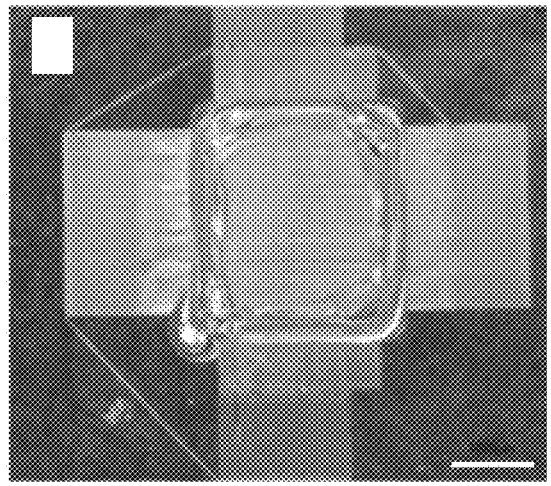
FIG. 1C depicts an example of a three-dimensionally printed (3DP) device, in accordance with aspects of the present invention.
Figure 1D:
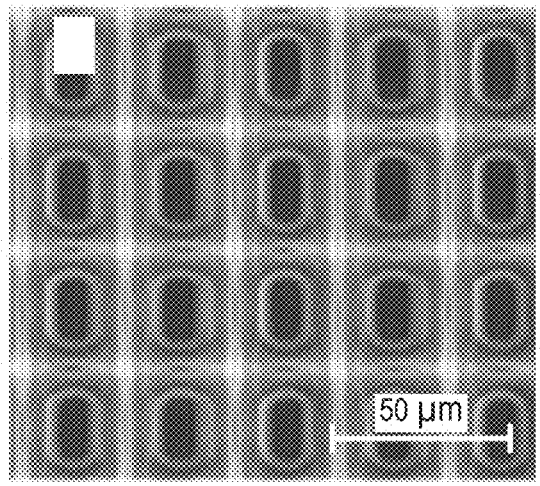
FIG. 1D depicts a higher magnification of the device pictured in FIG. 1C.
Figure 1E:
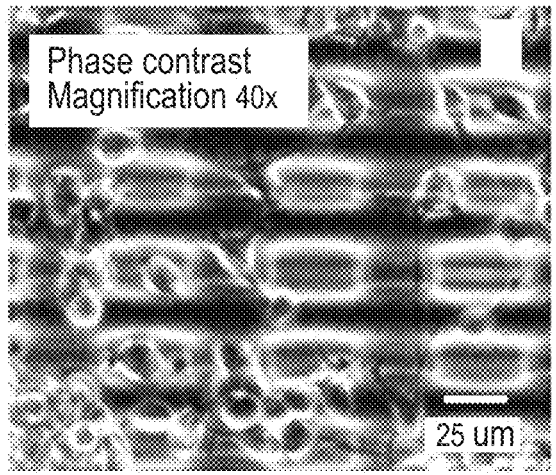
FIG. 1E depicts oligodendrocyte precursor cells (OPCs) attaching to and migrating on a polyHEMA neuron mimetic device of 10 μm fiber diameter, in accordance with aspects of the present invention.
Figure 1F:
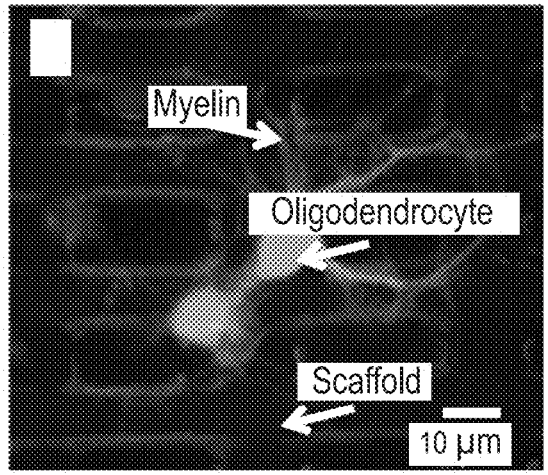
FIGS. 1F and 1G depict cells differentiated into oligodendrocytes and wrapping neuron mimetic fibers with layers of myelin, in accordance with aspects of the present invention.
Figure 1G:
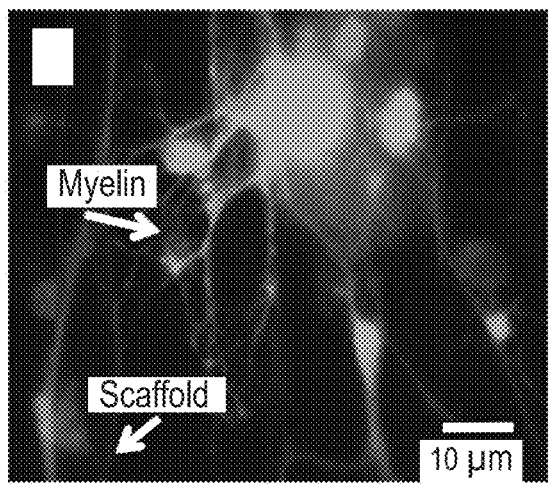

FIG. 1C depicts an example of the 3DP device consisting of four layers of polyHEMA (polyhydroxyethylmethacrylate) fibers of material elastic modulus 100 kPa, diameter of 10 µm, and spacing of 20 µm between fibers. A rim printed of polydimethylsiloxane (PDMS) creates the well for fluid culture media. FIG. 1D shows a higher magnification of the device pictured in FIG. 1C.

FIG. 1E shows how oligodendrocyte precursor cells (OPCs) can attach to and migrate on a polyHEMA neuron mimetic device, shown with 10 µm fiber diameter. FIGS. 1F-G show OPCs cultured in the device, differentiated into oligodendrocytes, and wrapping the neuron mimetic fibers with layers of myelin.

Figure 1H:
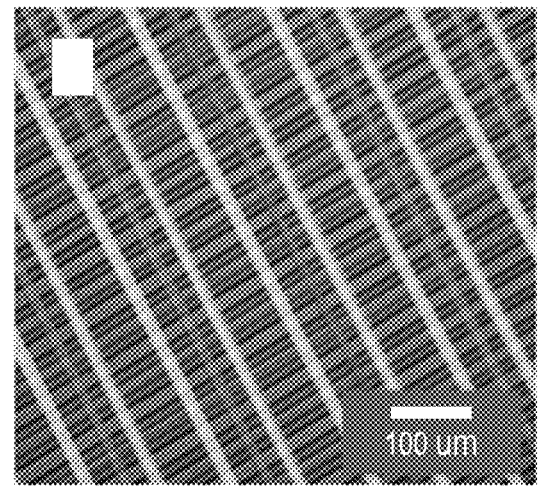
FIG. 1H depicts an example of a multimaterial scaffold, consisting of two types of polyHEMA fibers of 10 μm diameter, having different stiffnesses, in accordance with aspects of the present invention.

FIG. 1H depicts a multimaterial scaffold, consisting of two types of polyHEMA fibers of 10 µm diameter, with fiber-material Young's elastic modulus of E~2.7 kPa (green) and 4.5 kPa (red).

In some embodiments, 3D printing is done using compliant fibers with desired small diameters and low stiffness, using, for example, optimized fiber material properties and selected printing parameters. For example, in one embodiment, for HEMA-based inks, the list of varied components include:

pHEMA (1,000,000 Da)
pHEMA (300,000 Da)
HEMA monomer
Water
PBS without Ca and Mg
Glycerol
Ethanol
EGDMA (comonomer)
Lysine
DMPA (initiator)
Irgacure (initiator)spacing
Fibrinogen (340,000 Da)
Xanthum Gum (filler)
Nile Blue
Rhodamine In other embodiments, aspects of the invention relate to printing structurally stable fibers with very low stiffness, at very small diameters, e.g., low stiffness of fibers while maintaining small diameter. One example of a pHEMA formulation is as follows: 10 wt % 1 MDa pHEMA, 25 wt % 300 kDa pHEMA, 5 wt % HEMA monomer, 33.5 wt % water, 1 wt % EGDMA, 25 wt % ethanol, and 0.5 wt % irgacure; printed in a humid environment; and cured post-printing. This can result in fine features (down to 1 µm in diameter) with a low final cured stiffness (1.5 kPa).

Feature Gradients

In some embodiments, properties of cell mimetics are constant over a region of space (e.g., over the device). In other embodiments, one or more properties vary over a region of the device. The region over which the variation occurs can be a volume region, area region, or linear (segment) region. For example, a volume region can be defined by a cube having a linear dimension of 1 µm, 5 µm, 10 µm, 20 µm, 50 µm, 100 µm, 200 µm, 500 µm, 1 mm, 2 mm, 5 mm, or 10 mm per edge; an area region can be defined by a square having, per side, any of the foregoing linear dimensions; and a linear (segment) region, can have any of the foregoing linear dimensions. The region could also be defined, for example, as a fraction of a linear dimension of the device, for example, 1%, 5%, 10%, 25%, or 50%, with corresponding area and volume regions being defined by the fraction in two, or three, device dimensions, respectively.

Average properties can be calculated within one or more subregions within the regions, and changes in average properties from one subregion to the next can be calculated. For example, the region can be divided along each available dimension into, for example, 3 parts—yielding 3 subregions for a linear region, 9 subregions for an area region, and 27 subregions for a volume region. In other examples, the region can be divided into 2, 4, 5, 8, 10, 20, 50, or 100 parts per available dimension.

In some embodiments, changes in average properties are reported as a gradient within the region (e.g., as a rate of change in an average property of subregions across a linear dimension within the region). In some embodiments, the gradient is such that one or more properties change by a factor of, for example, about 1.1, 1.3, 1.5, 2, 5, 10, 50, 100, or 500 across the region.

For example, there can be a gradient of one or more properties (e.g., diameter of fibers from which cell mimetic is formed, stiffness of fibers, density of fibers, composition of fibers, surface density of a chemical or biochemical surface marker or modifier). In some embodiments, the cell-mimetic (e.g., axon mimetic) incorporates gradients of material stiffness, axon diameter, and/or ligand presentation. In some embodiments, e.g., those using 3D printing, these features are easily "tuned" during construction of the device, allowing for the facile construction of custom assemblies. Such assemblies can be, for example, models of generically healthy or generic disease states, or more specifically, models of a disease state or region in an individual subject (e.g., human patient) or a tissue/cellular region thereof.

In some embodiments, 3DP can enable construction of biochemical and mechanical gradients within printed fibers or among an array of printed fibers that will serve as the neuron mimetic. Such gradients are often present in both healthy and diseased environments and strongly affect responses of other CNS cell types (Jagielska et al., 2012, Jagielska et al., 2013). In accordance with aspects of the invention, 3DP structures incorporate tunable gradients of material stiffness, axon diameter, and ligand presentation.

Figure 2A:
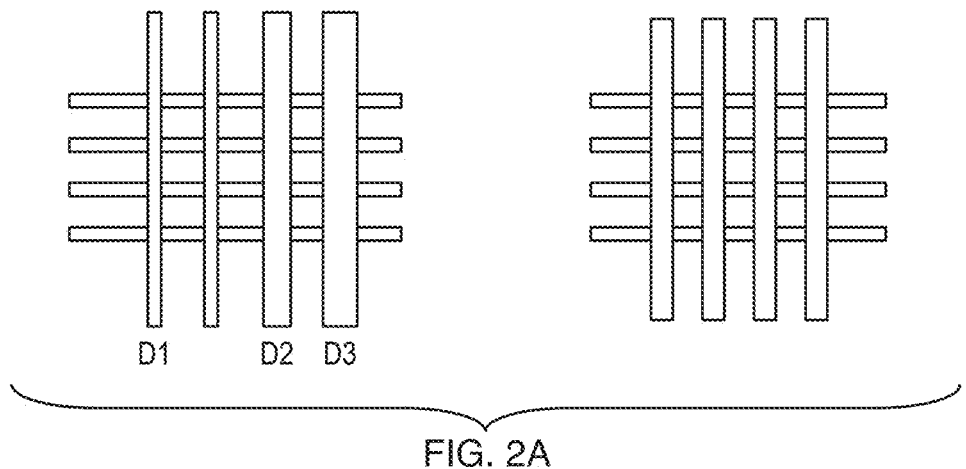
FIG. 2A is schematic representation of gradients incorporated into fiber devices, in accordance with aspects of the present invention, namely gradients of fiber diameter.
Figure 2B:
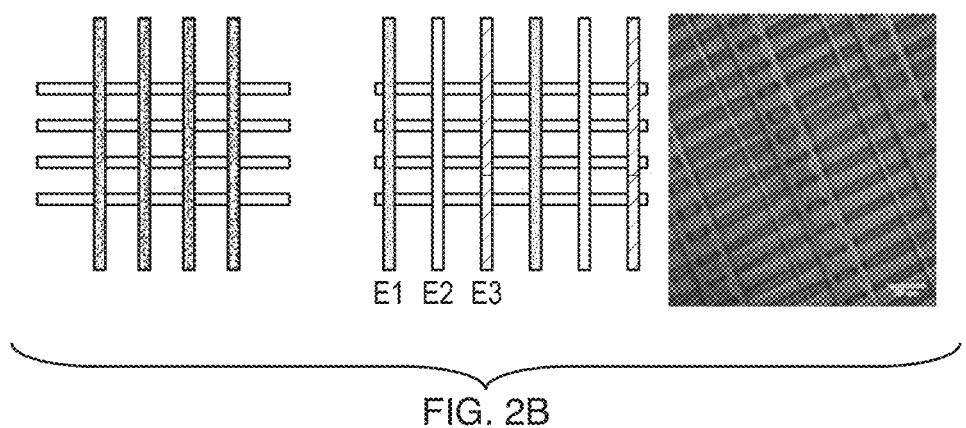
FIG. 2B is a schematic representation of gradients incorporated into fiber devices, in accordance with aspects of the present invention, namely gradients of fiber stiffness, with E1-E3 representing different Young's moduli.
Figure 2C:
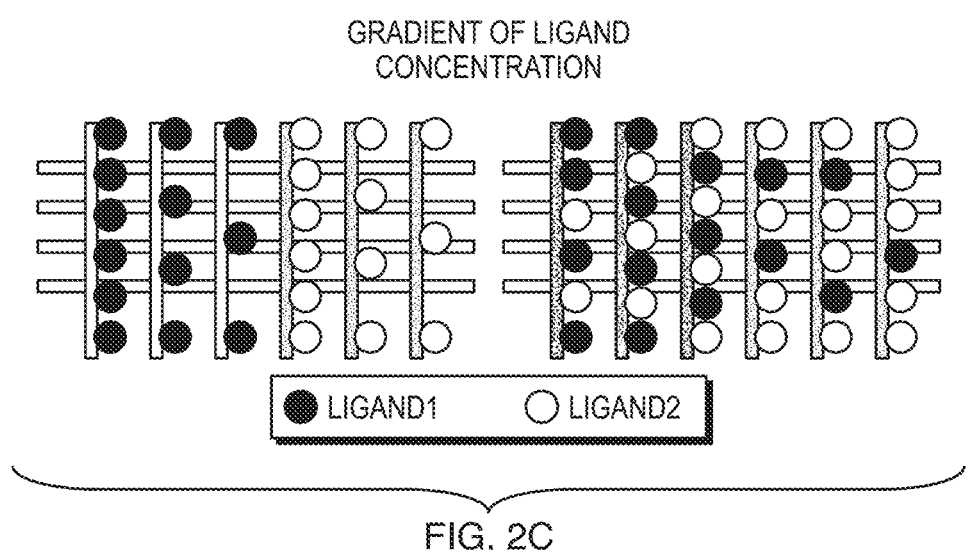
FIG. 2C is a schematic representation of gradients of ligand concentration in accordance with aspects of the present invention, with red and blue dots representing two different ligands.

In some embodiments, the invention relates to incorporating pre-designed, well controlled gradients, created by fibers with different features, such as gradients of fiber diameter (FIG. 2A), fiber stiffness (FIG. 2B), and ligand density (FIG. 2C) presented to a cell that is in contact with the neuron-mimetic fibers. In FIG. 2B, E1-E3 represent different Young's moduli, and in FIG. 2C, red and blue dots represent two different ligands.

Applications of Cell Mimetics

Cell/tissue mimetic structures (e.g., neuron mimetics) according to aspects of the present invention can be used in a wide variety of applications, including, without limitation for the following:

(a) in vitro investigation of disease, e.g., neurological diseases (e.g., demyelinating disease, multiple sclerosis);

(b) in vitro study of interactions of cells with the cell/tissue mimetic structure, and/or with other cells and cell types within an environment of the cell mimetic structure, including:

(1) how the interaction is modified by the application of one or more substances (e.g., drugs);

(2) for neuron-mimetics, an in vitro study of myelination of axons (represented by the printed fibers) by other neural cell types; and (c) high-throughput drug screening for cells adhered within the cell-mimetic architecture and environment (e.g., within neuron-mimetic architecture).

Stretchable Embodiments

This invention also includes a subset of cell mimetics (e.g., 3DP neuron mimetics) that are stretchable, such as, for example by using a stretchable version of the printed fibers. This can be used to enable a study of the effects of strain on neuronal cells. Here, the length and diameter of the artificial axon will change as a function of strain applied to the entire device. This can enable a controlled study of these physical cues on the adherent glial cells' response, e.g., by using devices to study such mechanical strain effects in architectures and environments similar to neural tissue. The roles of the natural and pathological strains (e.g., those associated with axon growth, myelin wrapping, or axon swelling due to inflammation) in CNS development and diseases can thereby be studied.

Stretchable Artificial Axons.

Some embodiments relate to a stretchable version of axon mimetic devices, by printing the stretchable fibers, made of polydimethylsiloxane elastomer (PDMS), inside depressed wells of stretchable PDMS plates.

Figure 3A:
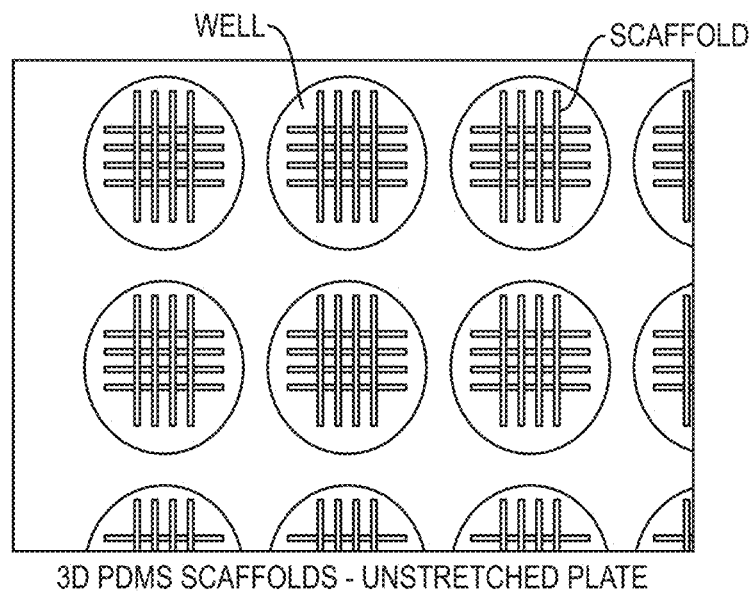
FIG. 3A shows a schematic representation of a stretchable log pile structure printed in wells of a stretchable PDMS plate, in accordance with aspects of the present invention.
Figure 3B:
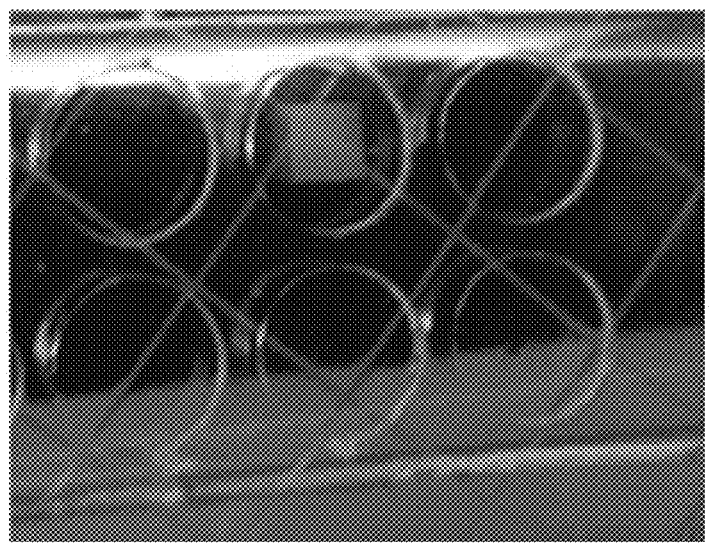
FIG. 3B shows an image of a PDMS printed scaffold within the well of PDMS stretchable plate, in accordance with aspects of the present invention.
Figure 3C:
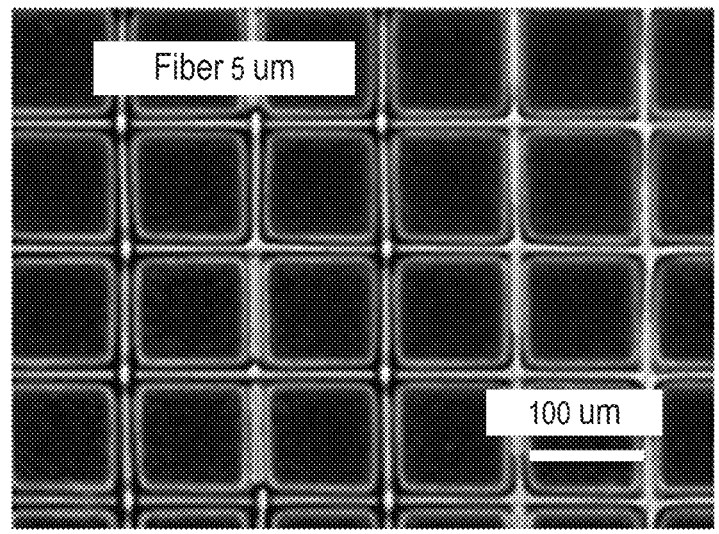
FIG. 3C shows a magnified scaffold with a fiber diameter of 5 μm, and a 100 μm spacing between fibers, in accordance with aspects of the present invention.
Figure 3D:
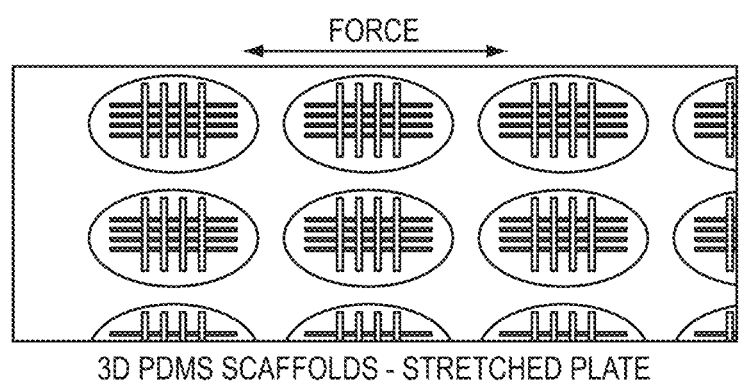
FIG. 3D shows a schematic representation of a stretched plate and scaffolds, in accordance with aspects of the present invention.
Figure 3E:
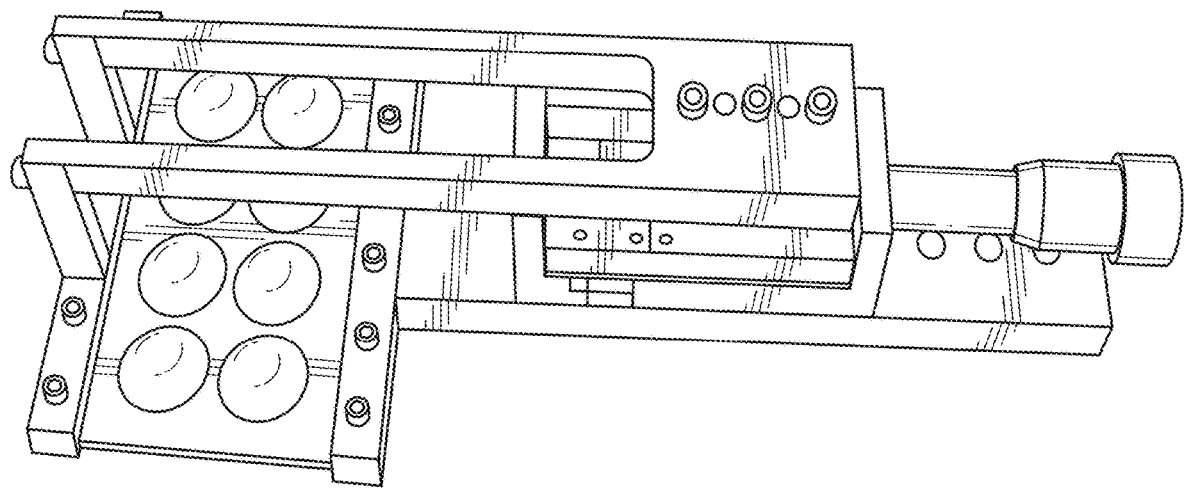
FIG. 3E shows a stretchable plate mounted on a stretcher device, in accordance with aspects of the present invention.
Figure 3F:
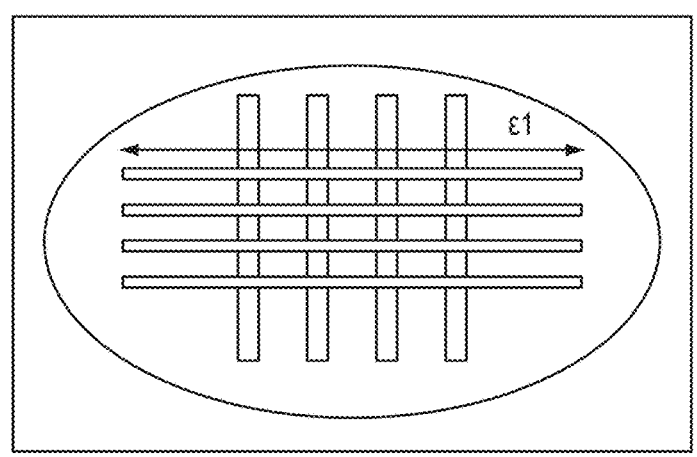
FIG. 3F shows a strain of 10% applied to a PDMS plate, the strain being transferred to the fiber scaffold, in accordance with aspects of the present invention.
Figure 3G:
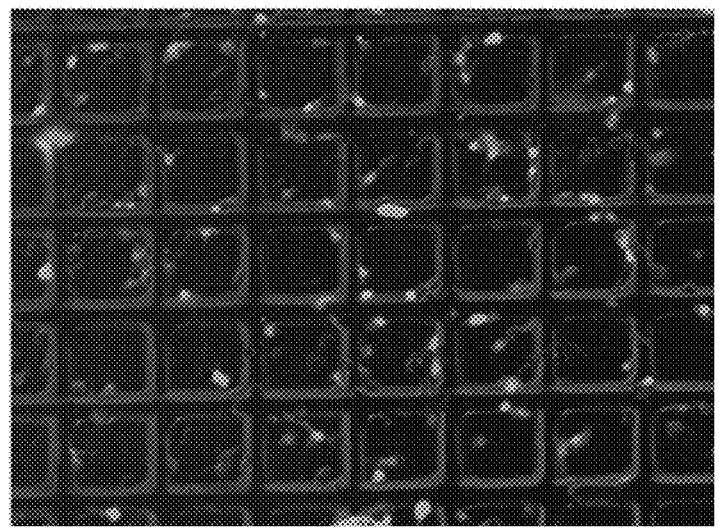
FIG. 3G shows oligodendrocyte producing cells (OPCs) (green) adhered to the PDMS scaffold (red), in accordance with aspects of the present invention.
Figure 3H:
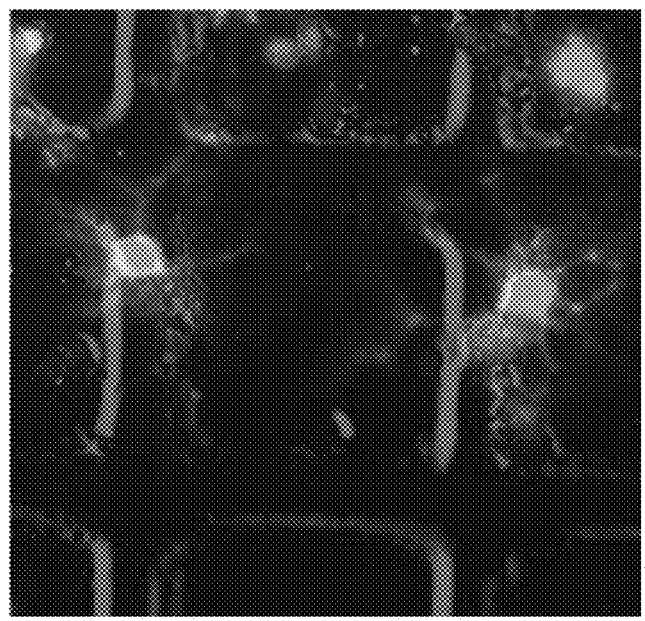
FIG. 3H shows differentiated oligodendrocytes (green) on a PDMS scaffold (red), in accordance with aspects of the present invention.

FIG. 3A depicts a schematic representation of a stretchable log pile structure printed in wells of the stretchable PDMS plate. FIG. 3B shows an image of the actual printed axon fiber structure. FIG. 3C shows a magnified structure with fiber diameter of 5 µm and 100 µm spacing between fibers. FIG. 3D is a schematic representation of a stretched plate and axon fiber structure. FIG. 3E is a stretchable plate mounted on a stretcher device. FIG. 3D depicts a strain of 10% applied to the PDMS plate, efficiently transferred to the axon fiber structure, resulting in an average strain $\varepsilon 1=10\%$ (elongation of the fibers in the direction of applied strain). FIG. 1G shows OPCs (green) adhered to the PDMS axon fiber structure (red). FIG. 3H shows differentiated oligodendrocytes (green) on the PDMS axon fiber structure (red). Green fluorescence in cells is generated by green fluorescent protein (GFP) fused to myelin basic protein (MBP)—the differentiation marker expressed in oligodendrocytes.

In some embodiments the invention relates to a PDMS custom-made plate (e.g., 6-well), wherein in each well is printed multiple layers of PDMS fibers, covering an area, e.g, 3 mm×3 mm area. PDMS fibers can be covalently functionalized with poly-D-lysine or surface ligands that are present in a neural environment in vivo (fibronectin, laminin). These PDMS plates can include, for example, those developed in the Van Vliet lab at MIT (see Zeiger 2013), and can be stretched by applying uniaxial tensile strain with a customized strain device developed in the Van Vliet lab at MIT (see, e.g., FIGS. 3D, 3E).

It was confirmed via optical microscopy that strain applied to the plate is transferred completely to the 3DP neuron mimetic printed within each well, resulting in elongation of the 3DP fibers in the direction of applied force (FIG. 3F), and that the decrease of diameter of fibers aligned with the strain axis. It was demonstrated that OPCs thrive on these PDMS-based 3DP neuron mimetic devices, and differentiate into oligodendrocytes that wrapped the fibers with myelin. These devices can be used to quantify the effect of strain in 3D environments on oligodendrocyte differentiation, to gain better understanding of how physiological and pathological strains contribute to this process, and how such dynamic changes in axon properties can affect drug metabolism and response. Therefore, in some embodiments, the invention relates to a compliant axon mimicking device allowing the study of effects of axonal strain on glial cell biology.

Assay for Quantification of Myelination.

Myelin production during human development, and stimulation of myelin repair (remyelination) in demyelinating diseases such as multiple sclerosis, are central unsolved problems in neuroscience and neuromedicine. The current lack of a facile, adaptable, and high throughput assay to compare myelin production or repair efficacy under conditions mimicking in vivo environments is considered a major obstacle to progress in therapy development. The recently developed assay for myelination (Mei et al., 2014, Chan and Lee, 2014) although providing high throughput myelin quantification, uses glass as a cell substrate, which is orders of magnitude stiffer than nervous tissue, therefore providing very different mechanical cues than those present in vivo.

In some embodiments, this invention relates to a version of an artificial axon device for use in a myelination assay. In some embodiments, the assay enables a simultaneous imaging of fiber cross-section to quantify myelin thickness and fiber length to quantify length of myelin segment. In other embodiments, each is measured separately or at different times/orientations of the device. Fibers with a range of different mechanical or/and biochemical properties can be provided in a single assay, e.g., to represent healthy and pathological axons. In some embodiments, drugs/compounds are added to enable quantification of myelination in response to those drugs/compounds, such as, for example, in different mechanical/biochemical conditions representative of a disease. Moreover, arranging the fibers with different mechanical/biochemical properties such that they recreate in vivo mechanical/biochemical gradients can be used to investigate the impact of gradients on myelination.

Figure 4A:
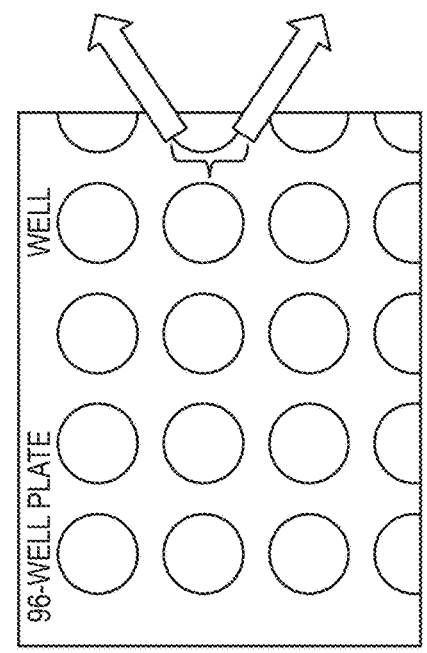
FIG. 4A shows a schematic of a 3DP neuron mimetic myelination device, which includes a multi-well plate.
Figure 4B:
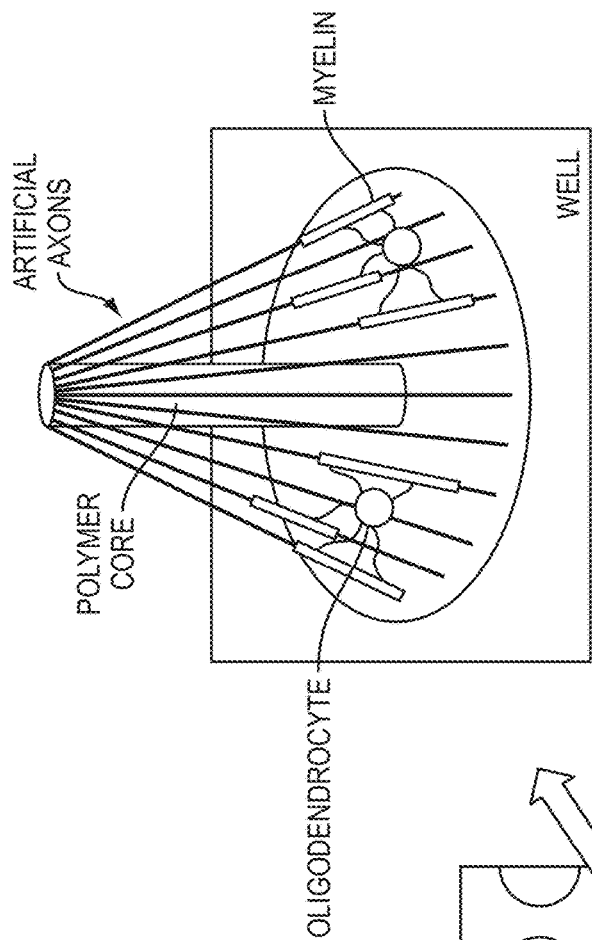
FIG. 4B shows a schematic of structure (in one example) within a single well within the multi-well plate, according to aspects of the present invention.
Figure 4C:
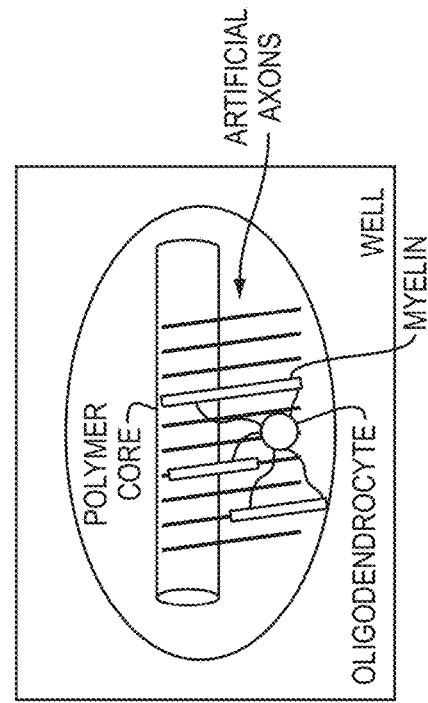
FIG. 4C shows a schematic of structure (in another example) within a single well within the multi-well plate, according to aspects of the present invention.
Figure 5A:
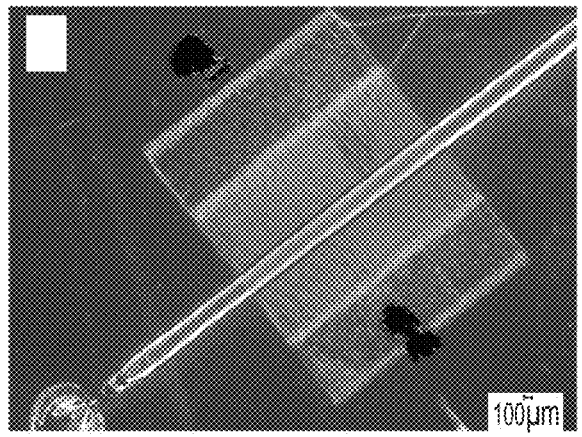
FIG. 5A depicts a myelination assay device according to aspects of the present invention.
Figure 5B:
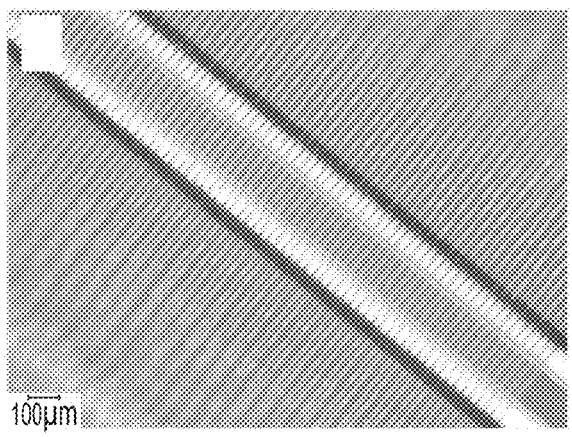
FIG. 5B depicts a magnification of the device from FIG. 5A
Figure 5C:
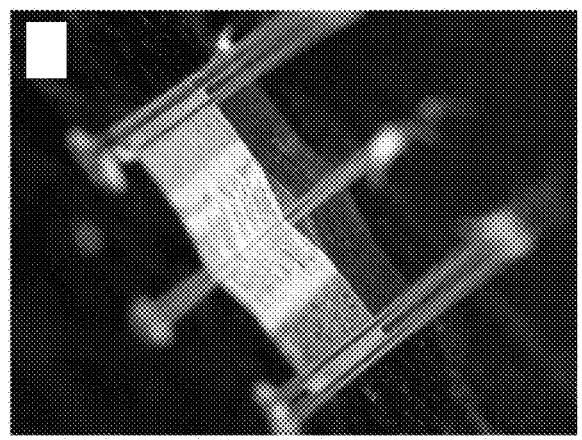
FIG. 5C provides another view of the device.
Figure 5D:
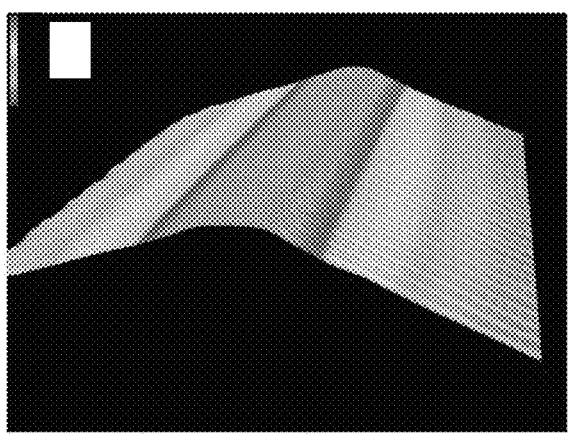
FIG. 5D provides an image of suspended fibers with colors scale corresponding to height above glass slide surface, according to aspects of the present invention.

FIG. 4 shows an example of a device used in connection with aspects of the invention, a 3DP neuron mimetic myelination device. Shown in FIG. 4A is a schematic of a multi-well plate. FIGS. 4B and 4C show two examples of a schematic of a single well within a multi-well plate. Oligodendrocytes grow in the plate well (green) in the vicinity of polymer artificial axon-fibers, representing different biophysical features of an axon such as stiffness, diameter, or ligand presentation, relevant to different disease environments. The extent of fiber myelination by oligodendrocytes can vary depending on these conditions, allowing for discrimination between environments beneficial or detrimental for myelination. Drug screening in a multi-well plate format of this device can be performed, allowing, for example, assessment of drug effects in a multiplexed platform.

For example, a 3DP axon mimetic approach can be used to create a biomimetic myelination assay that takes advantage of uniform fiber geometry to facilitate rapid quantification of myelin thickness and segment length, while providing compliant axon-like polymer fibers with diversity of ligand coatings. The device can consist of a multi-well plate (e.g., 6, 12, 24, 48, 96, 384-well), wherein each well contains multiple polymer axon-mimicking printed fibers (FIG. 4). The fibers can, for example, have low stiffness mimicking that in vivo, and in some embodiments can be anchored at the top of a stiffer supporting polymer core. In some embodiments, they can maintain an angled, extended position despite the mechanical compliance of the fiber material (two examples of fiber arrangements on the supporting core are shown, FIG. 4). Use of optically transparent polymers (e.g., PEG (polyethylene glycol), PDMS or poly-HEMA) and this angled fiber geometry can allow for simultaneous acquisition of fluorescent images of myelin rings on the fiber cross-section to assess myelin thickness, and the assessment of size of myelin segment (e.g., length) on each fiber via optical microscopy, to conduct rapid quantification of myelination amount and distribution.

With reference to FIG. 5, a prototype of a 3DP neuron mimetic myelination device is shown. FIG. 5A depicts a myelination assay device consisting of a PDMS support beam (length: 10 mm, height 0.4 mm) printed on the glass slide and pHEMA fibers that are attached to the glass support slide along 1 mm of the fiber lengths, on both sides of the beam, whereas the fiber middle section (2 mm) is suspended in air and span over the PDMS beam. FIG. 5B depicts a magnification of the device from FIG. 5A. FIG. 5C shows an image of the device through the bottom of the glass slide, to visualize suspended fibers over the central beam; top and bottom PDMS beams stamp fibers to the glass slide. FIG. 5D shows an image of the suspended fibers with color scale corresponding to height above glass slide surface. pHEMA was UV cured and PDMS was thermally cured at 80° C. for 2 h.

In some embodiments of the device, each fiber can be printed according to a specific design to represent different biological conditions of an axon, such as stiffness, diameter, or ligand expression. This presents OPCs grown in the plate well with various, controlled biological conditions, and the cells will choose the biological conditions that are optimal for myelination, by myelinating some types of fibers more than others (which is not possible with other assays that provide one type of pillar or fiber material). The same myelination assay can be performed after application of a drug and multiplexed in all wells of the plate to test effects of different drug compositions and dosages on myelination efficiency. Therefore, this device embodiment enables simultaneous high throughput drug screening and testing of drug effects in different biological conditions, represented by fibers with different characteristics.

In some embodiments, the myelination assay involves one or any combination of the following:
  uses different materials—biocompatible, biomimetic polymer fibers (PEG, pHEMA, PDMS) that are similar to real axons in their stiffness and diameters. This can provide an advantage over assays that use etched glass micropillars (or other stiff plastics), which are orders of magnitude stiffer than real axons, and may not represent the axon mechanical environment correctly.
  has a geometry designed to maintain suspended compliant fibers at the angle sufficient to image simultaneously the fiber cross-section and length for rapid myelin quantification, e.g. wherein the beginning and the end of the suspended section of the fiber defines a line segment having an angle to the substrate surface of about 5°, 10°, 10°, 20°, 30°, 45°, 50°, 60°, 70°, 80°, or 85°. This can provide an advantage over assays using stiff micropillars vertically rising from the glass surface, and of cross-sectional geometry that is not constant along the pillar length.
  enables the creation in a single assay of combinations of fibers with diverse mechanical and biochemical properties that represent a complex disease environment, such as local changes in axon stiffness or ligands expressed on an axon surface. This allows for studying drug responses in credible biomimetic environments that are fully controlled and reproducible.

Other aspects of some embodiments include, alone, or in any combination, the following:
  Biocompatible, neuronal axon mimetic (fiber) with tunable diameter and stiffness within the range of biological neural cell properties.
  Suitable for research on myelin diseases.
  Amenable to oligodendrocyte precursor cell culture, adhesion, and differentiation to produce myelin.
  Enables study of axon myelination of fibers, advantageous over 2D dish format.
  Enables high throughput myelination assay of drug responses in complex, designable mechano/biochemical environments that mimic real disease microenvironments.
  Suitable for research on a wide spectrum of neuronal diseases that involve axons—amenable to cell culture of other glial cells that interact with axons (microglia, astrocytes).
  3D-printing of fibers with a wide range of stiffness, including very low stiffness of 0.1-1 kPa characteristic of nervous tissue.
  3D-printing of gradients of fiber length, diameter and/or mechanical stiffness, controllable within a single printed device footprint.
  3D-printing of multi-molecular compositions/molecular gradients, controllable presentation within a single printed device footprint.
  Enables separation of mechanical and biochemical cues on myelination and other processes involving axons, which is not possible to separate in tissue slice cultures.
  Enables creation of mechanical and biochemical gradients by design, to mimic the disease environment features expected in tissue.
  Mechanical and biochemical variation can be introduced independently, at the level of single fibers (axons) or entire fiber network (tissue).
  Suitable for research on the effect of strain in neurological diseases—amenable to mechanical stretching and modulation of fiber diameter as described.

Novel printing materials—improved 3DP ink formulations for hydrogels and UV-curable elastomers (PEG-, pHEMA, PDMS-based inks).

Provides potential to study effects of dynamic change of axon diameter on myelination, which is not possible with existing devices.

Provides high throughput, low cost in vitro drug screening assays for axon/myelin associated diseases.

Additional Embodiments

In some embodiments, the "artificial axon device" consists of axon mimicking fibers, which can have various stiffness within the range corresponding to stiffness of neural tissue and neural cells, 0.1-1 kPa, and stiffness above 1 kPa.

In some embodiments, the axon fibers can have a range of diameters of micrometer scale, including a range of 0.1-20 micrometers.

In some embodiments, the axon fibers can have different molecules and molecule densities on their surface.

In some embodiments, the biomimetic fibers can be produced from various compliant polymers and hydrogels, including PEG, pHEMA, PDMS, and poly-acrylamide, and their derivatives. The fibers are arranged in a predefined order to create a desired representation of the disease microenvironments.

In some embodiments, methods/devices can be used to screen/investigate drugs/therapies/candidates or create models/model the progression of disease, e.g., demyelinating disease, multiple sclerosis.

Such arrangements can include gradients of properties, such as fiber stiffness, ligand density on the fiber surface, and fiber diameter. Such arrangements can be achieved by e.g., various 3D printing methods (including direct printing.)

In some embodiments, the invention relates to a device in the "stretchable artificial axon" form. In this version of the device, the fibers described above can be printed from a stretchable material (e.g. PDMS or pHEMA), and deposited on a stretchable medium (e.g. PDMS plate where the fibers are printed in each well of the plate), which facilitates stretching of the fibers using external stretching device.

In some embodiments, fibers are printed in geometries that include a supporting polymer core and compliant fibers spanning the distance from the device bottom to the top of the core, such that the angle between fibers and the device bottom is sufficient to enable simultaneous microscope imaging of both the fiber cross-section and fiber length. Such geometry allows for fast quantification of myelin thickness and length to enable fast screening for myelin drugs in various disease conditions represented by different mechanical and biochemical properties of the fiber arrangements.

In some embodiments, pharmaceutical companies developing drugs for neurological diseases, especially those working on remyelination therapies and myelin diseases (e.g., multiple sclerosis), can use devices and methods described herein.

In some embodiments, devices are multiplexed, such as multi-well plates (e.g., 6, 12, 24, 48, 96, 384-well plates), petri dishes, glass or plastic slides.

In some embodiments, the invention relates to materials optimized for 3D printing. These include PEG-, pHEMA, PDMS, and poly-acrylamide based materials optimized for 3D printing.

The teachings of all patents, published applications and references cited herein, incorporated by reference herein in their entirety.

Also incorporated herein and forming a part of this application is the material attached hereto as an appendix.

While this invention has been particularly shown and described with references to example embodiments thereof, it will be understood by those skilled in the art that various changes in form and details may be made therein without departing from the scope of the invention encompassed by the appended claims.

REFERENCES

Barry, R. A., Shepherd, R. F., Hanson, J. N., Nuzzo, R. G., Wiltzius, P. & Lewis, J. A. Direct-Write Assembly of 3D Hydrogel Scaffolds for Guided Cell Growth. Adv. Mater. 21, 2407-2410, doi:10.1002/adma.200803702 (2009).

Chan, J., Lee, S. Patent WO 2014/100199 A1 "Micropillar arrays for assaying myelination".

Hanson-Shepherd J, Parker S T, Shepherd R F, Gillette M U, Lewis J A, and Nuzzo R G, 3D Microperiodic Hydrogel Scaffolds for Robust Neuronal Cultures, (2011), Adv. Funct. Mater., 21, 47-54.

Jagielska A, Norman A L, Whyte G, Vliet K J, Guck J, Franklin R J, Mechanical Environment Modulates Biological Properties of Oligodendrocyte Progenitor Cells, (2012), Stem Cells Dev., November 1; 21(16):2905-14.

Jagielska A, Wilhite K D, Van Vliet K J, Extracellular Acidic pH Inhibits Oligodendrocyte Precursor Viability, Migration, and Differentiation, (2013), PLoS ONE 8(9): e76048. doi:10.1371.

Kolesky, D. B., Truby, R. L., Gladman, A. S., Busbee, T. A., Homan, K. A. & Lewis, J. A. 3D Bioprinting of Vascularized, Heterogeneous Cell-Laden Tissue Constructs. Adv. Mater. 26, 3124-3130, doi:10.1002/adma.201305506 (2014).

Lee, S., Leach, M. K., Redmond, S. A., Chong, S. Y., Mellon, S. H., Tuck, S. J., Feng, Z. Q., Corey, J. M. & Chan, J. R. A culture system to study oligodendrocyte myelination processes using engineered nanofibers. Nat. Methods 9, 917-922, doi:10.1038/nmeth.2105 (2012).

Li, Y., Ceylan, M., Shrestha, B., Wang, H., Lu, Q. R., Asmatulu, R. & Yao, L. Nanofibers support oligodendrocyte precursor cell growth and function as a neuron-free model for myelination study. Biomacromolecules 15, 319-326, doi:10.1021/bm401558c (2014).

Mei, F., Fancy, S. P., Shen, Y. A., Niu, J., Zhao, C., Presley, B., Miao, E., Lee, S., Mayoral, S. R., Redmond, S. A., Etxeberria, A., Xiao, L., Franklin, R. J., Green, A., Hauser, S. L. & Chan, J. R. Micropillar arrays as a high-throughput screening platform for therapeutics in multiple sclerosis. Nat. Med., doi:10.1038/nm.3618 (2014).

Sun, L, S T Parker, D Syoji, X Wang, J A Lewis, and D L Kaplan. 2012. Direct-Write Assembly of 3D Silk/Hydroxyapatite Scaffolds for Bone Co-Cultures, Advanced Healthcare Materials, no. 1: 729-735.

Zeiger A S, Ph.D. thesis, Chemomechanics at Cell-Cell and Cell-Matrix Interfaces Critical to Angiogenesis, (2013), Department of Materials Science and Engineering, Massachusetts Institute of Technology.

What is claimed is:

1. A cell-mimetic device comprising:
 a three-dimensional structure comprising a plurality of fibers composed of polyhydroxyethylmethacrylate (pHEMA), said plurality of fibers configured to mimic neuronal axons and having an average stiffness post-curing of between about 0.1 and about 300 kPa and an average diameter of between about 0.1 and about 50 micrometers; and a support structure connected to the three-dimensional structure; wherein the stiffness is calculated as any of Young's modulus, bulk modulus, shear modulus, and dynamic modulus; and post-curing stiffness is measured after equilibration in an aqueous solution buffered at pH 7.0-7.4.

2. The device of claim 1, wherein the post-curing stiffness is between about 0.1 and 100 kPa.

3. The device of claim 1, wherein the post-curing stiffness is between about 0.1 and 10 kPa.

4. The device of claim 1, wherein the post-curing stiffness is between about 0.1 and 1 kPa.

5. The device of claim 1, wherein the average diameter is between about 0.1 and about 10 micrometers.

6. The device of claim 1, wherein the average diameter is between about 0.1 and about 1 micrometers.

7. The device of claim 1, wherein the fibers are modified by a surface ligand.

8. The device of claim 1, wherein the average stiffness is constant over the three-dimensional structure.

9. The device of claim 1, wherein the average diameter is constant over the three-dimensional structure.

10. The device of claim 7, wherein a surface ligand density or a surface ligand type is constant over the three-dimensional structure.

11. The device of claim 7, wherein the plurality of fibers are arranged as one or more piles in the three dimensional structure, and at least one of fiber diameter, fiber stiffness, surface ligand density, and surface ligand type varies along at least one dimension of the three dimensional structure.

12. The device of claim 1, wherein the pHEMA fibers in the three-dimensional structure are stretchable.

13. The device of claim 12, wherein the three-dimensional structure is elastically deformable in at least one dimension by at least 5%.

14. The device of claim 13, further comprising a substrate material attached to, and at least as elastically deformable in the at least one dimension as, the three-dimensional structure.

15. A method of studying cells in vitro, comprising:
providing a three-dimensional structure comprising:
a plurality of fibers composed of polyhydroxyethylmethacrylate (pHEMA), said plurality of fibers configured to mimic neuronal axons and having an average stiffness post-curing of between about 0.1 and about 300 kPa and an average diameter of between about 0.1 and about 50 micrometers, and
a support structure connected to the three-dimensional structure;
providing a cell-mimetic device comprising a three-dimensional structure comprising a plurality of fibers;
contacting the cell-mimetic device with a population of cells;
studying at least one feature of an interaction of the population of cells with the cell mimetic device; and
studying at least one feature of an interaction between cells of the same cell type or of different cell types within the cell-mimetic device.

16. The method of claim 15, wherein the cells are neural cells or oligodendrocytes.

17. An assay device comprising:
a substrate;
a fiber support attached to the substrate; and
a plurality of fibers composed of polyhydroxyethylmethacrylate (pHEMA) and configured to mimic neuronal axons, each of the plurality of fibers having a length and spanning from the substrate to the fiber support such that each fiber is suspended in air or fluid along at least part of the fiber length, and the plurality of fibers having:
an average stiffness of between about 0.1 and about 300 kPa; and
an average diameter of between about 0.1 and about 50 micrometers; wherein the stiffness is calculated as any of Young's modulus, bulk modulus, shear modulus, and dynamic modulus;
and
wherein the post-curing stiffness is measured after equilibration in an aqueous solution buffered at pH 7.0-7.4.

18. The device of claim 17, wherein the fibers are modified by a surface ligand.

19. The device of claim 17, wherein the average stiffness is constant over the three-dimensional structure.

20. The device of claim 17, wherein the average diameter is constant over the three-dimensional structure.

21. The device of claim 18, wherein a surface ligand density or a surface ligand type is constant over the three-dimensional structure.

22. The device of claim 18, wherein the plurality of fibers are arranged as one or more piles in the three-dimensional structure and at least one of fiber diameter, fiber stiffness, and surface ligand density and type varies along at least one dimension of the three dimensional structure.

23. The device of claim 17, wherein the pHEMA fibers in the three-dimensional structure are stretchable.

24. An assay method comprising:
given the device of claim 17:
contacting the assay device with a population of cells; and
studying at least one feature of an interaction of the population of cells with the device.

25. The assay method of claim 24, wherein the cells are oligodendrocytes and the at least one feature of the interaction is myelination of the plurality of fibers.

26. The assay method of claim 25, wherein the studying comprises determining, for at least one of the plurality of fibers, both an extent of myelination along a longitudinal axis of the fiber and a thickness of myelin.

27. The assay method of claim 26, wherein the longitudinal extent and thickness of myelin are determined from microscopy images.

* * * * *